United States Patent [19]

Yamada

[11] Patent Number: 5,005,596
[45] Date of Patent: Apr. 9, 1991

[54] ARTIFICIAL HAIR FOR HAIR-IMPLANTATION AND PREPARATION PROCESS

[76] Inventor: Shiro Yamada, No. 2-7-1-606, Mita, Minato-ku, Tokyo, Japan

[21] Appl. No.: 352,447

[22] Filed: May 16, 1989

[30] Foreign Application Priority Data

Aug. 4, 1988 [JP] Japan ................... 63-193445

[51] Int. Cl.$^5$ ........................................ A41G 5/00
[52] U.S. Cl. ..................... 132/201; 132/53; 132/56; 623/15
[58] Field of Search ............ 132/53, 56, 200, 201; 623/15

[56] References Cited

U.S. PATENT DOCUMENTS

| | | | |
|---|---|---|---|
| 3,003,155 | 10/1961 | Mielzynski et al. | 132/53 |
| 3,119,398 | 1/1964 | Bennett et al. | 132/201 |
| 3,786,822 | 1/1974 | Kimura et al. | 132/53 |
| 4,004,592 | 1/1977 | Yamada | 623/15 |
| 4,144,876 | 3/1979 | DeLeo | 623/15 |
| 4,517,997 | 5/1985 | Forchetti | 132/201 |
| 4,588,408 | 5/1986 | Yamada | 623/15 |
| 4,793,368 | 12/1988 | Yamada | 132/201 |

FOREIGN PATENT DOCUMENTS

| | | | |
|---|---|---|---|
| 3539490 | 5/1987 | Fed. Rep. of Germany | 623/15 |
| 52-37153 | 3/1977 | Japan | 132/201 |
| 142704 | 4/1979 | Japan | |
| 2045089 | 10/1980 | United Kingdom | 623/15 |

*Primary Examiner*—John J. Wilson
*Assistant Examiner*—F. LaViola
*Attorney, Agent, or Firm*—Browdy and Niemark

[57] ABSTRACT

Artificial hair for hair-implantation, which is composed of a monofilament of a synthetic resin, wherein amorphous silver is adhered in spots to the surface of the monofilament by vacuum depositing said silver of the monofilament.

4 Claims, 4 Drawing Sheets

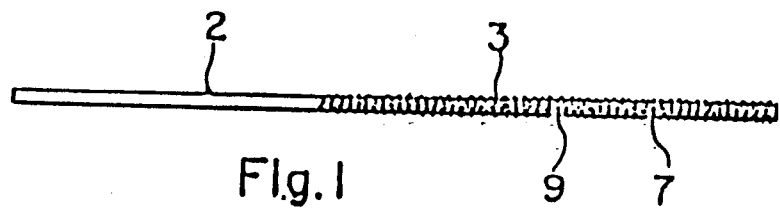
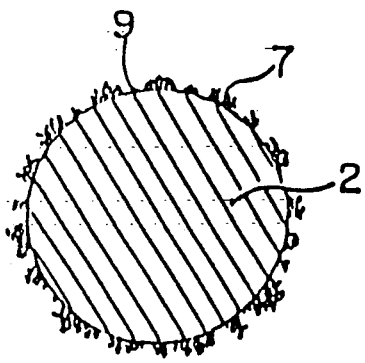
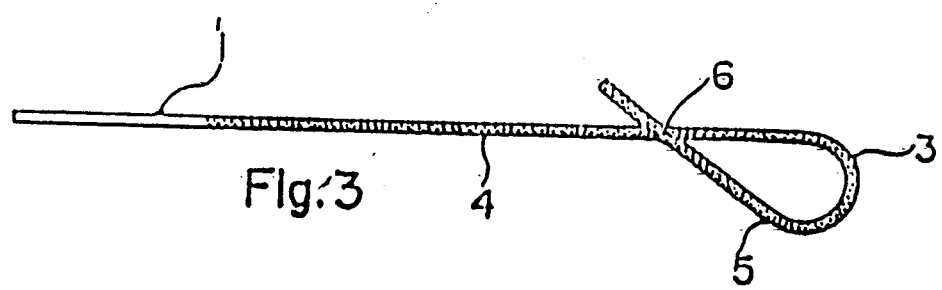
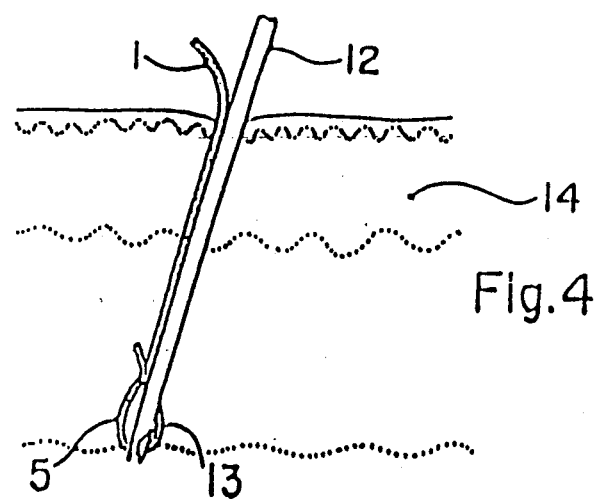

ARTIFICIAL HAIR FOR HAIR-IMPLANTATION AND PREPARATION PROCESS

The present invention relates to an artificial hair to be implanted directly in the human skin, and particularly to an artificial hair with a function for inhibiting the proliferation of bacteria imparted to its hair root part, which is to be inserted into the human skin, and a portion of its hair shaft part, which is adjacent to the hair root part, and a preparation process and a preparation apparatus thereof.

BACKGROUND OF THE INVENTION

It has been known to implant directly artificial hair, which is composed of a synthetic resin monofilament and have a hair root part at its end part, in the human skin.

DESCRIPTION OF THE RELATED ART

It has also been proposed to cause a metal such as gold, silver or copper to adhere in the form of a thin film to the surface of such artificial hair by vacuum deposition so as to impart sterilizing effects thereto, thereby inhibiting the infection of bacteria and the purulence caused by bacteria upon hair implantation (see Japanese Patent Laid-Open No. 142704/1980).

However, gold is innoxious to human body but has no sterilizing and bacteriostatic effects. Copper has sterilizing and bacteriostatic effects but is noxious to human body. Both gold and copper are hence unsuitable for applying to the artificial hair with a view toward inhibiting the purulence caused by bacteria. Silver is innoxious to human body and also has the sterilizing and bacteriostatic effects.

The above known method is still insufficient for reasons as will be described below.

PROBLEMS SOUGHT FOR SOLUTION BY THE INVENTION

In the above known artificial hair, which has caused the metal such as gold, silver or copper to adhere in the form of a thin film to the surface of its hair root part by vacuum deposition, it appears that the metal is deposited under the conventional vacuum deposition conditions, namely, a vacuum degree of $10^{-7}$ Torr or higher and a surface temperature of an artificial hair to be deposited, i.e., a substrate temperature, of 60°-80° C. In this case, the metal 11 deposited forms a uniform layer in a crystalline state on the entire surface of the artificial hair 10 as illustrated as a conventional example by FIG. 8.

Here, the vacuum deposition, which has generally been performed, is described in further detail. In the conventional vacuum deposition apparatus 20, a vacuum vessel 21 is mounted on a fixing frame 35, which is fixed on a base stand 40, via a packing 34 as depicted in FIG. 9. An opening for an exhaust pipe 36 communicating with the vacuum vessel 21 is defined through the upper surface of the base stand 40. To the exhaust pipe 36, a vacuum pump 26 is connected through an oil trap 28, an oil diffusion pump 27, an exhaust conduit 41 and a three-way cock 29. In addition, a bypass line 42 branches off from the exhaust pipe 36 to be connected with the vacuum pump 26 through another three-way cock 30. On one hand, a crucible 23 equipped with a heater is attached to the fixing frame 35 by a crucible-supporting arm 31. In the vacuum vessel 21, a rotary body 22 adapted to fix a substance to be deposited is rotatably attached to a supporting arm 38 through a rotating shaft 37. A back heater 25 for heating the substance to be deposited is positioned on the side of the back surface of the rotary body 22.

Incidentally, reference numbers 24, 32, 33 and 43 are indicative of a shutter adapted to shade the flying of metal particles which evaporates, a driving chain for rotating the rotary body 22, a wire adapted to lift the vacuum vessel 21 and an electric wire for supplying electric power to the heater of the crucible 23, respectively.

In order to conduct vacuum deposition by means of this apparatus, the substance to be deposited is first of all attached on the rotary body 22, a depositing metal, for example, silver is placed in the crucible 23, the vacuum vessel is covered on, and the vacuum pump 26 is then driven to exhaust air in the vacuum vessel 21. At this time, the three-way cock 30 is opened first and the three-way cock 29 is turned on the side of the bypass line 42 to exhaust the air in the vacuum vessel 21 through the bypass line 42. When the vacuum degree of the vacuum vessel becomes about $10^{-5}$ Torr, the three-way cock 30 is closed and the three-way cock 29 is turned on the side of the oil diffusion pump 27. The oil diffusion pump 27 is then actuated. As the vacuum degree becomes $10^{-7}$ Torr or higher, the silver in the crucible 23 is heated to its melting temperature (961.9° C.) or higher by the heater.

On one hand, the substance to be deposited, namely, a monofilament of a synthetic resin is heated by the back heater 25 to maintain the temperature of the substrate at 60°-70° C. (the temperature is different depending on the kind of a substance to be deposited).

Since particles of the silver start to discharge as the silver melts, the shutter 24 is opened to run the particles into the substance to be deposited, thereby forming a deposited film of the silver in a crystalline form on the surface of the substance to be deposited. The thus-formed deposited film of the crystalline silver has a metallic luster, i.e., a silver color. Furthermore, the surface of the deposited film is flat and its surface area is hence smallest.

In general, when a metal is contacting with the dermal tissue of the human body, a larger amount of the metal ion dissolves out in the skin as the contact surface becomes greater. Therefore, when following the conventionally-known method, the amount of the metal ion which dissolves out in the skin is extremely little and sterilizing and bacteriostatic action is also little correspondingly.

SUMMARY OF THE INVENTION

It is an object of the present invention to provide an artificial hair for hair-implantation, which has a hair root part extremely high in bacteriostatic effects and innoxious to human body, and a preparation process and a preparation apparatus thereof.

If a metal layer is coated on the surface of a monofilament composed of a thermoplastic synthetic resin prior to the formation of the hair root part, it is difficult to wind and fusion-bond an end part of the monofilament in order to form the hair root part and to fusion-bond a hair root part formed separately to the end part of the monofilament due to the presence of the metal layer.

It is another object of the present invention to provide an artificial hair, which does not interfere with the formation of a hair root part by fusion bonding even when the metal layer for a sterilizing action is caused to adhere in advance to the surface of the artificial hair, and a preparation process and a preparation apparatus thereof.

MEANS FOR THE SOLUTION OF THE PROBLEMS

The present inventor has carried out an extensive investigation with a view toward achieving the above-mentioned objects. As a result, it has been found that amorphous silver has outstanding effects on sterilizing and bacteriostatic action compared with silver, which has been caused to adhere uniformly in a crystalline form, leading to completion of the present invention.

Namely, the artificial hair for hair-implantation according to this invention is composed of a synthetic resin monofilament which has caused amorphous silver to adhere in spots to the surface thereof.

In order to obtain such an artificial hair for hair-implantation, amorphous silver is caused to adhere in spots to the surface of an artificial hair, which is composed of a monofilament of a synthetic resin such as polyamide, polyethylene or polyester, by subjecting the artificial hair to vacuum deposition of silver at a vacuum degree of $10^{-3}$–$10^{-6}$ Torr, preferably $10^{-4}$–$10^{-5}$ Torr and a substrate temperature of 36° C. or lower, preferably room temperature (about 20° C.).

Incidentally, if the vacuum degree is lower than $10^{-3}$ Torr, it is impossible to perform the vacuum deposition due to so-called poor vacuum degree.

With respect to the substrate temperature, any temperatures not higher than 36° C. may be used. However, it is most preferable to control its temperature to about 20° C. because no particular change is recognized on effects even when the temperature is controlled to 0° C. or lower. On the contrary, facilities for controlling to such a low temperature become very complicated. In the case of silver, when the substrate temperature is higher than 36° C., amorphous silver can not be formed but a film of crystalline silver is formed.

It is preferable to control a degree of adhesion of the amorphous silver in spots, namely, a proportion of the adhesion area of the amorphous silver to the surface area of the synthetic resin monofilament, which is to be subjected to vacuum deposition, to 20–80%. Any proportions lower than 20% result in an artificial hair having less sterilizing and bacteriostatic effects. On the contrary, any proportions higher than 80% render the exposed area of the synthetic resin small, whereby difficulty is encountered on the formation of the hair root part by the fusion bonding.

In order to control such a degree, the period of time of the vacuum deposition and/or the amount of the depositing silver may be adjusted. The simplest method is to determine its degree by the color density of the amorphous silver deposited. Namely, this method comprises determining the relationship between the deposited amount of the amorphous silver and the color density in advance to prepare an optimum sample so as to stop the vacuum deposition as the color of the artificial hair turns into the same color as that of the sample.

Furthermore, the present inventor has improved on the conventional vacuum deposition apparatus with a view toward obtaining such an artificial hair for hair-implantation, leading to the development of an apparatus for depositing amorphous silver in spots at a time on the end parts of numerous monofilaments composed of a synthetic resin. This apparatus comprises a vacuum vessel communicating with a vacuum pump via an on-off valve, a crucible provided in the vacuum vessel and equipped with a heater for fusing silver for deposition, and a rotary container provided in the vacuum vessel and adapted to receive numerous monofilaments composed of a synthetic resin therein and to rotate. The above-mentioned rotary container is formed in the shape of a hollow cylinder and provided with an opening defined individually in close vicinity to both ends or one end thereof so as to cause silver particles coming flying to deposit on the corresponding both or one end parts of the monofilaments of a desired synthetic resin.

The above rotary container in the form of a hollow cylinder is provided with small projections arranged at equal spaces along the circumferential direction on the inner surface thereof so as to serve to hook, lift and stir the monofilaments of the synthetic resin upon the rotation of the rotary container. In order to stir the numerous monofilaments of the synthetic resin while keeping them parallel, it is preferable to provide with the small projections in parallel rows. It is possible to coat equally with the amorphous silver on the end parts only of the numerous monofilaments in such a manner as described above. Moreover, it has been possible to obtain an artificial hair for hair-implantation, which is high in fixity after implantation thereof and excellent in sterilizing and bacteriostatic effects, by causing the amorphous silver to adhere in spots to the end surface of the thermoplastic synthetic resin monofilament by the vacuum deposition, winding the thus-deposited end part and then fusion-bonding an intersection of the thus-wound end part and a hair shaft part by high-frequency spot welding, thereby forming a hair root part in an α-shape.

EFFECTS

When subjected to vacuum deposition of silver under conventional conditions, for example, a vacuum degree higher than $10^{-6}$ Torr, crystalline silver 11 uniformly adheres on a substance to be deposited as illustrated in FIG. 8, thereby forming an extremely flat surface on the substance. When subjected to vacuum deposition of silver at a vacuum degree of $10^{-3}$–$10^{-6}$ Torr and a substrate temperature of 36° C. or lower on the other hand, amorphous silver is deposited in spots. Since the amorphous silver is in a porous and irregular form as depicted in FIG. 2, its surface area is thousands times compared with that of the crystalline silver. Therefore, when the artificial hair according to this invention, which has caused the amorphous silver to adhere in spots, is implanted in the skin, a silver ion which dissolves out in the subcutaneous tissue increases by leaps and bounds, so that sterilizing and bacteriostatic effects attributed to such a silver ion become extremely high. Furthermore, since the artificial hair according to this invention is caused to adhere with the amorphous silver in spots, the surface of the thermoplastic synthetic resin monofilament is partly exposed. It is accordingly possible to fusion-bond a hair root part to a hair shaft part by a welding technique or the like so as to join them and to wind the end part of the monofilament and then fusion-bond an intersection of the thus-wound end part and a hair shaft part so as to form a hair root part. In addition, since the amorphous silver has a pale brown color well similar to that of natural hair, it does not look strange even if the amorphous silver is caused to adhere to an artificial hair. Moreover, when used in an artificial hair for white hair by way of example, the appearance of natural hair is rather given as the hairline of the artificial hair implanted becomes pale brown. By the way, amorphous gold has a purple color and amorphous copper exhibits a green color. It is hence unsuitable to use both amorphous gold and copper as a deposit for the artificial hair even from the viewpoint of color.

BRIEF DESCRIPTION OF THE DRAWINGS

FIG. 1 is a monofilament of a synthetic resin having amorphous silver adhered in spots, and in the state before the formation of the hair shaft part.

FIG. 2 is a sectional view a part of the monofilament of FIG. 1.

FIG. 3 is a prospective view of artificial hair having a hair root in the α-shape.

FIG. 4 depicts the application of the artificial hair according to the invention.

EXAMPLES

FIG. 1-FIG. 4 illustrate the embodiment of the artificial hair in accordance with the present invention, wherein FIG. 1 shows an monofilament of a synthetic resin, which has caused amorphous silver to adhere in spots and is in the state before the formation of its hair shaft part, FIG. 2 is a sectional view of a part of the monofilament in FIG. 1, FIG. 3 is a perspective view of an artificial hair having a hair root part in an α-shape and FIG. 4 depicts an application example of the artificial hair according to this invention.

In FIG. 1, a reference number 2 indicates the monofilament of the synthetic resin, which has caused the amorphous silver to adhere in spots to the surface of an end part 3 thereof. The amorphous silver 7 is in a porous and irregular form as illustrated by the sectional view in FIG. 2. The formation of such amorphous silver may permit by controlling the vacuum degree and substrate temperature to $10^{-3}$–$10^{-6}$ Torr, preferably $10^{-4}$–$10^{-5}$ Torr and 36° C. or lower, preferably room temperature, respectively, upon subjecting the monofilament of the synthetic resin to deposition of silver by means of a conventional vacuum deposition apparatus. It is considered that the vacuum deposition under such conditions forms the amorphous silver in spots because silver particles evaporated by heating the silver irregularly move due to turbulence of the flying locus of the silver particles, which is caused by residual gas molecules, at that time when the silver particles are about to adhere to the surface of the substance to be treated so as to form crystalline silver.

DESCRIPTION OF PREFERRED EMBODIMENTS

Figure 5:
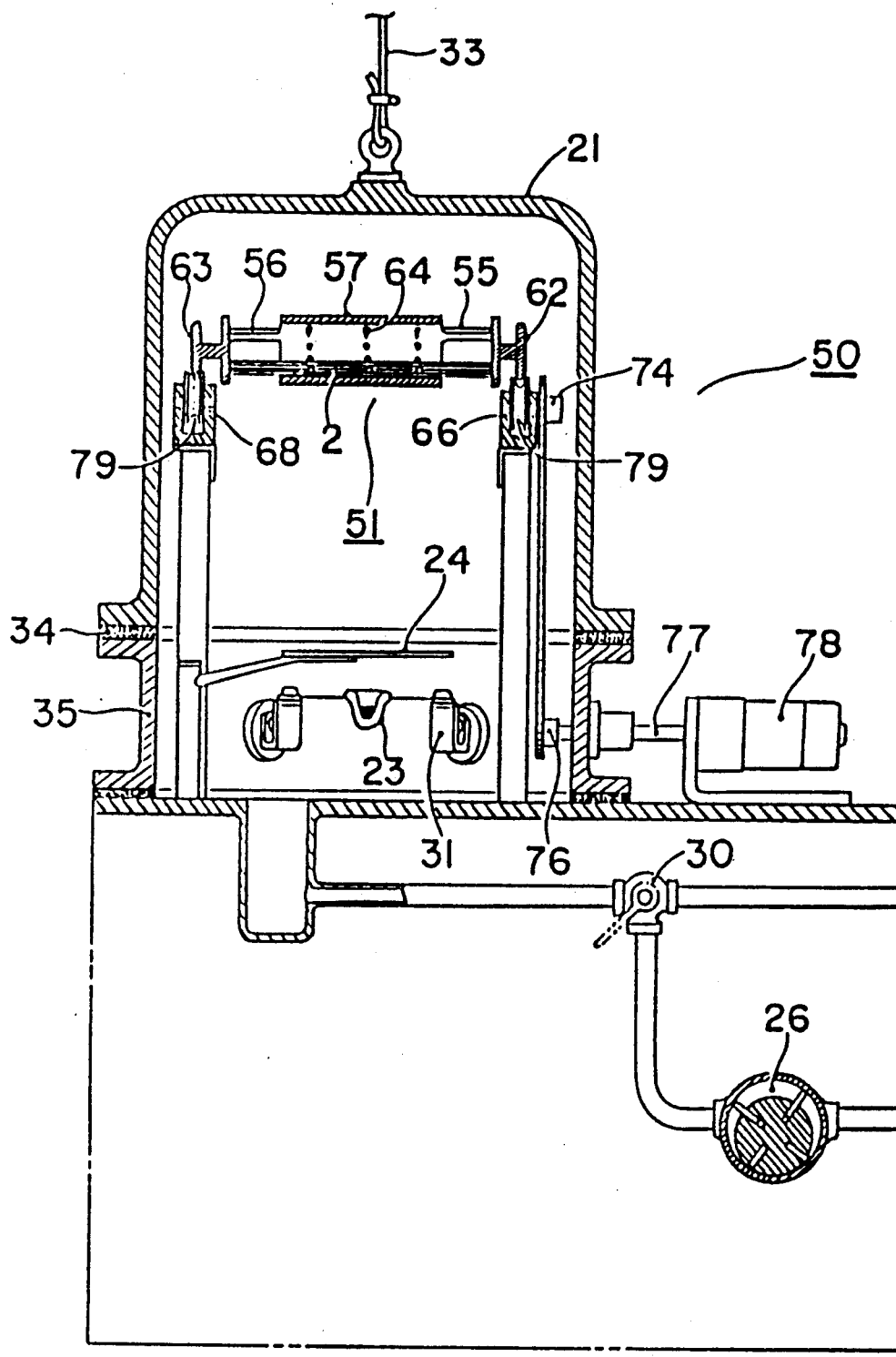
FIG. 5 shows the vacuum deposition apparatus according to the invention.

The production process according to this invention will now be described specifically referring to the vacuum deposition apparatus as illustrated in FIG. 5.

Figure 9:
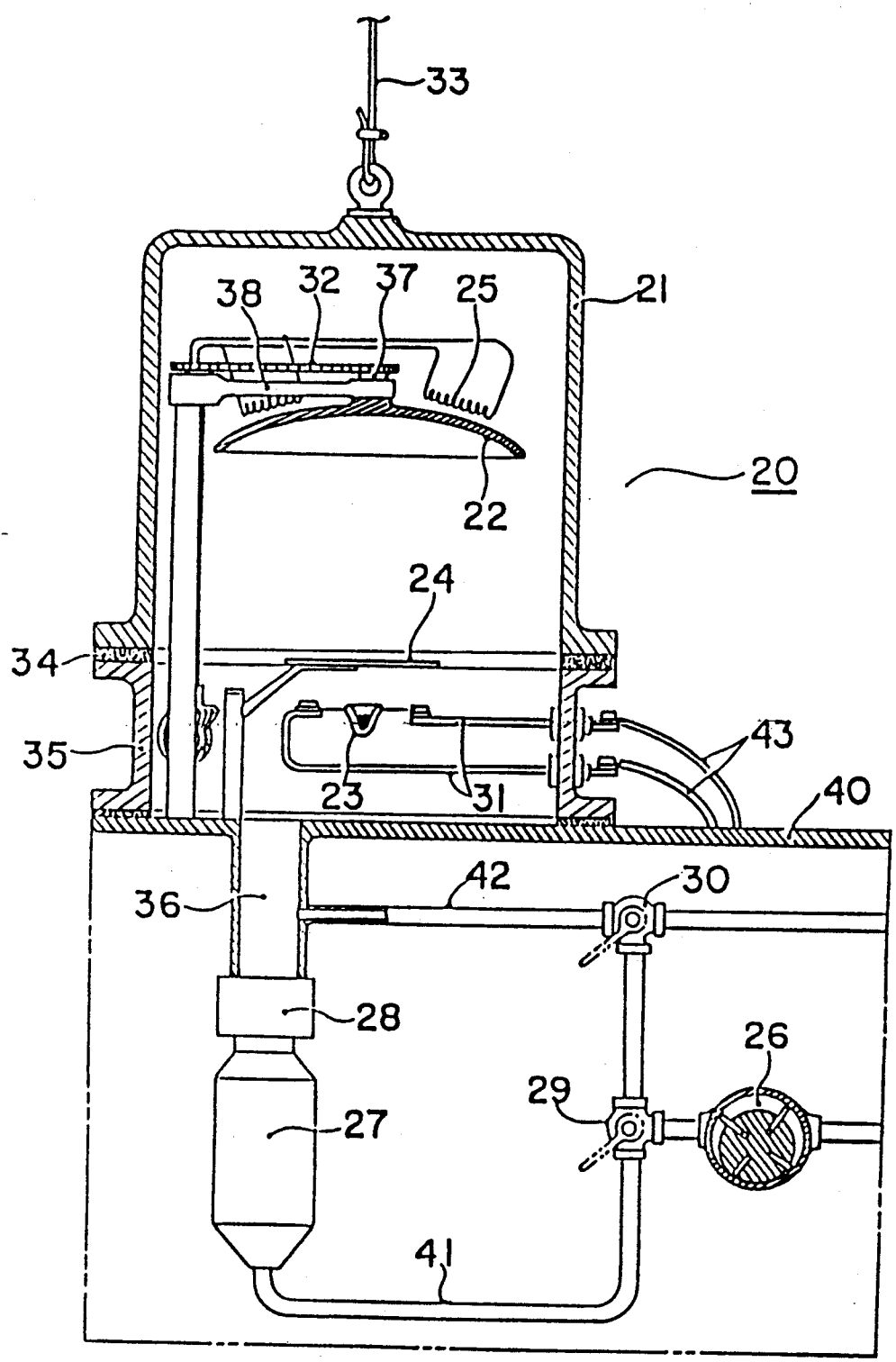
FIG. 9 shows the whole body of conventional vacuum deposition apparatus.

The vacuum deposition apparatus 50 of the present invention as illustrated in FIG. 5 differs from the conventionally-known vacuum deposition apparatus 20 as depicted in FIG. 9 in that it is provided with a particular rotary container for holding artificial hairs in place of the rotary body 22 in the conventional apparatus in order to deposit amorphous silver on both end parts of numerous artificial hairs at a time, the oil diffusion pump 27 and the oil trap 28 are omitted because it need not generate a vacuum degree higher than $10^{-6}$ Torr, and the back heater 25 is eliminated as it is unnecessary to heat the substance to be deposited. The other points are almost the same.

Figure 6:
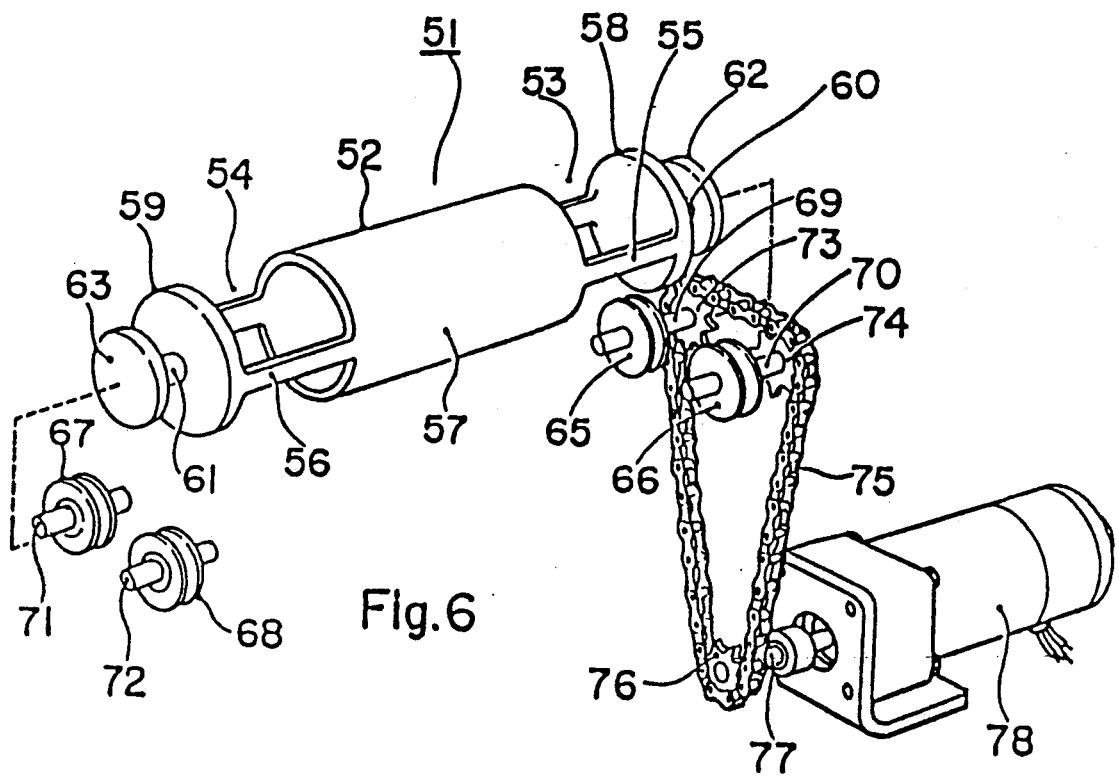
FIG. 6 is an enlarged prospective view of a part of the rotary container.
Figure 7:
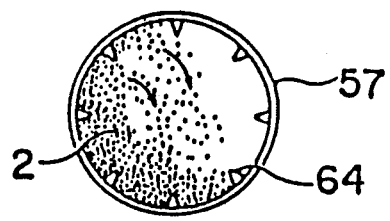
FIG. 7 is a sectional view of the rotary container.
Figure 8:
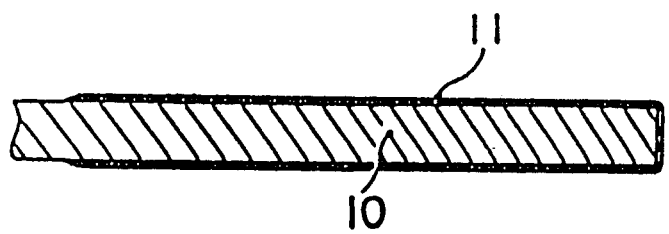
FIG. 8 is a sectional view of conventional artificial hair.

Namely, in FIG. 5-FIG. 7, the particular rotary container 51 for holding the artificial hairs 2 is formed of a hollow cylinder 52 both ends of which are closed, and is provided with openings 53 and 54 defined in close vicinities to said both ends of the hollow cylinder 52. Some joints 55 and 56 are separately provided in order to join the center part 57 of the hollow cylinder 52 to said both ends 58 and 59. Center shafts 60 and 61 are respectively fixed in said both ends 58 and 59, to the tips of which rotating wheels 62 and 63 are fixed respectively. Small projections 64 are provided in rows in the interior of the rotary container 51, particularly, on the inner surface of the center part 57 so as to lift and stir the artificial hairs 2 contained in the interior upon the rotation of the rotary container 51 so that silver equally deposits on the intended surfaces of the artificial hairs.

The rotating wheels 62 and 63 provided on both ends of the rotary container 51 are mounted respectively on two pairs of pulleys 65, 66 and 67, 68 provided in an opposing relation therewith. All the pulleys 65-68 are provided with a concave groove 79 to prevent the rotating wheels 62, 63 from deviating.

Rotating shafts 69 and 70, which are inserted loosely and rotatably in suitable bearing means, are fixed respectively to the pulleys 65 and 66. Sprockets 73 and 74 are fixed respectively to the sides opposite to the pulleys of the rotating shafts 69 and 70. A chain 75 driven by a driving sprocket 76 is stretched under tension on the sprockets 73, 74. The driving sprocket 76 is rotated by means of a motor 78 through a driving shaft 77.

Rotating shafts 71 and 72 fixed respectively to the pulleys 67 and 68 are inserted loosely and idlably in suitable bearing means.

In order to deposit silver on both end parts of the monofilaments for artificial hair using this apparatus, the silver 23 is first of all placed in a crucible 23. Two thousand of the monofilaments for artificial hair are contained in the rotary container 51. A vacuum vessel 21 is covered on, and a vacuum pump 26 is then actuated to increase a vacuum degree to $10^{-5}$ Torr.

On one hand, electricity is supplied to a heater provided in the crucible 23 to heat the crucible to 1000° C. or higher, thereby allowing the silver to melt. At that time, the temperature of a substrate sample, i.e., the monofilaments for artificial hair is the same as room temperature (for example, 20° C.).

As the motor 78 is actuated to rotate the driving sprocket 76, chain 75 and sprockets 73, 74, the rotary container 51 mounted thereon is rolled, whereby some of the monofilaments, artificial hairs 2 are lifted by the small projections 64 provided inside the rotary container 51 and then naturally fall again, so that the monofilaments are stirred. As a shutter 24 is opened at a suitable time, amorphous silver deposits on both ends of the artificial hairs exposed from the openings 53, 54 of the rotary container 51.

After portions deposited with the silver are formed on both end parts of a monofilament in such a manner as described above so as to make hair root parts at said both end parts, the monofilament is cut at its center, whereby two artificial hairs can be produced at one process.

In order to determine the degree of the deposition, some of white artificial hairs are mixed with the monofilaments in advance. When their color is compared with that of a standard sample prepeared in advance so that their colors are consistent, the shutter 24 is closed, thereby bringing to completion of the operation.

Using actually the above apparatus, an example for the embodiment of the process for the preparation of artificial hairs according to this invention will now be described.

Using the vacuum deposition apparatus equipped with the vacuum vessel having a diameter of 400 mm and a height of 400 mm, two thousand of synthetic resin monofilaments having a diameter of 0.095 mm and a black color were treated batchwise at a vacuum degree of $10^{-5}$ Torr and a substrate temperature of 20° C. (said monofilaments being treated for their portions to the extent of 5 cm from their both ends but the other portions thereof being covered with a shielding member). Incidentally, the time treated was 5 minutes and the amount of silver used was about 0.5 g. The portions deposited with amorphous silver had a dull black color, so that their color could not be almost distinguished from that of the other portions. The white artificial hairs which had been incorporated for the determination of color exhibited a pale brown color at their both end parts.

FIG. 3 shows an artificial hair according to this invention, which has been prepared from a monofilament for artificial hair by the process described above and has a hair root part in an α-shape.

The artificial hair 1 is prepared by winding an end part 3 of the monofilament 2 as illustrated in FIG. 1, which is composed of the thermoplastic synthetic resin and has caused the amorphous silver 7 to adhere in spots, and then fusion-bonding an intersecion 6 of the thus-wound end part and a hair shaft part 4 by high-frequency spot welding, thereby forming a hair root part in an α-shape. Incidentally, since the amorphous silver 7 adheres in spots as depicted in FIG. 2 and exposed portions 9 hence exist on the monofilament 2, the inter-monofilament can be fusion-bonded by the spot welding even when deposited with the silver, thereby forming the hair root part 5.

In order to apply the artificial hair 1 according to this invention, as illustrated in FIG. 4, the hair root part 5 in the α-shape of the artificial hair 1 is held by a hook 13 provided at the tip of a hair implanting needle 12 and then thrusted into the skin 4 by the needle 12 to implant the artificial hair 1. After the implantation, a fibrous connective tissue attributed to foreign body reaction is formed in the hole of the hair root part 5 in the α-shape to fix the artificial hair 1. With the artificial hair 1 implanted, a silver ion dissolves out of the amorphous silver 7, thereby inhibiting the infection of bacteria just after the hair-implantation. In addition, the silver ion semipermanently continue to dissolve out in the subcutaneous tissue, thereby producing sterilizing and bacteriostatic effects.

ADVANTAGES

Since the amorphous silver formed in spots on the surface of the synthetic resin monofilament is in a porous and irregular form, its surface area becomes extremely large. Therefore, with the artificial hair made of this material, an extremely large amount of a silver ion dissolves out in the subcutaneous tissue after the implantation of the artificial hair, thereby increasing its sterilizing and bacteriostatic effects correspondingly.

Moreover, since the amorphous silver is formed in spots and the surface of the thermoplastic synthetic resin monofilament is hence exposed partly, it does not interfere with the formation of the hair root part by the fusion bonding.

Since the amorphous silver formed in spots on the surface of the synthetic resin monofilament exhibits a pale brown color and hence has the same color as that of the natural human hair, no incompatible feeling is given even when using it for the artificial hair. The artificial hair according to this invention can therefore be used as is.

1... artificial hair, 2... monofilament, 3... end part, 5... hair root part, 6... intersection, 7... amorphous silver, 9... exposed portion, 10... artificial hair, 11... metal deposited, 12... hair implanting needle, 13... hook, 14... skin, 20... conventional vacuum deposition apparatus, 21... vacuum vessel, 22... rotary body, 23... crucible, 24... shutter, 25... back heater, 26... vacuum pump, 27... oil diffusion pump, 28... oil trap, 29, 30... three-way cocks, 31... crucible-supporting arm, 32... driving chain, 33... lift, 34... packing, 35... fixing frame, 36... exhaust pipe, 37... rotating shaft, 38... supporting arm, 40... base stand, 41... exhaust line, 42... bypass line, 43... electric wire, 50... vacuum deposition apparatus of the present invention, 51... rotary container, 52... hollow cylinder, 53, 54... openings, 55, 56... joints, 57... center part, 58, 59... ends, 60, 61... center shafts, 62, 63... rotating wheels, 64... small projection, 65, 66, 67, 68... pulleys, 69, 70... rotating shafts, 71, 72... rotating shafts, 73, 74... sprockets, 75... chain, 76... driving sprocket, 77... driving shaft, 78... motor, 79... concave groove.

What is claimed is:

1. In an artificial hair for hair-implantation, which is composed of a monofilament of a synthetic resin, the improvement wherein amorphous silver is adhered in spots covering about 20–80% of a distal end to surface of the monofilament by vacuum depositing said amorphous silver at between $10^{-3}$ to $10^{-6}$ Torr and at a monofilament temperature of 36° C. or lower.

2. A process for the preparation of an artificial hair for hair-implanation comprising, causing amorphous silver to adhere in spots by vacuum depositing said silver at between $10^{-3}$–$10^{-6}$ Torr to surfaces of said artificial hair composed of a monofilament of a synthetic resin.

3. The process for preparation of artificial hair for hair-implantation as claimed in claim 2, wherein the amorphous silver is caused to adhere in spots to the surface of the artificial hair by vacuum deposition of silver at a vacuum degree of $10^{-4}$–$10^{-5}$ Torr and a substrate temperature of 36° C. or lower.

4. A process for the preparation of an artificial hair for hair-implantation comprising, causing amorphous silver to adhere in spots to surfaces of an end part of a monofilament composed of a thermoplastic synthetic resin by vacuum depositing said silver at between $10^{-3}$–$10^{-6}$ Torr, winding the deposited end part and fusion-bonding an intersection of the wound end part and a hair shaft part by high frequency spot welding to form a hair root part in an α-shape.

* * * * *